United States Patent
Pfister (10) Patent No.: US 8,200,040 B2
(45) Date of Patent: Jun. 12, 2012

(54) IMAGE SYSTEM FOR RETAINING CONTRAST WHEN MERGING IMAGE DATA

(75) Inventor: Marcus Pfister, Bubenreuth (DE)

(73) Assignee: Siemens Aktiengesellschaft, München (DE)

( * ) Notice: Subject to any disclaimer, the term of this patent is extended or adjusted under 35 U.S.C. 154(b) by 966 days.

(21) Appl. No.: 12/150,950

(22) Filed: May 1, 2008

(65) Prior Publication Data

US 2008/0273784 A1      Nov. 6, 2008

(30) Foreign Application Priority Data

May 4, 2007  (DE) .................. 10 2007 021 035

(51) Int. Cl.
*G06K 9/36* (2006.01)
*G06K 9/00* (2006.01)
*G06K 9/40* (2006.01)
*G06K 9/32* (2006.01)
*G09G 5/00* (2006.01)
*H04N 9/74* (2006.01)

(52) U.S. Cl. ........ 382/284; 382/128; 382/131; 382/274; 382/294; 345/629; 348/584

(58) Field of Classification Search .................. 382/128, 382/131, 284, 294, 274; 345/629; 348/584
See application file for complete search history.

(56) References Cited

U.S. PATENT DOCUMENTS

| | | | | |
|---|---|---|---|---|
| 7,502,503 B2 * | 3/2009 | Bojer et al. | ..................... | 382/132 |
| 7,650,044 B2 * | 1/2010 | Kreang-Arekul et al. | .... | 382/274 |
| 7,873,909 B2 * | 1/2011 | Evans | ........................... | 715/764 |
| 8,050,471 B2 * | 11/2011 | Mielekamp et al. | .......... | 382/128 |
| 2007/0071341 A1 * | 3/2007 | Pfister | ........................... | 382/254 |
| 2007/0103483 A1 * | 5/2007 | Glen | ............................. | 345/592 |

FOREIGN PATENT DOCUMENTS

| DE | 103 04 703 A1 | 8/2004 |
|---|---|---|
| WO | WO 94/06111 A1 | 3/1994 |

OTHER PUBLICATIONS

Alfred Iwainsky, Wolfgang Wilhelmi; "Lexikon der Computergrafik und Bildverarbeitung"; Vieweg Verlagsgesellschaft, 1994, p. 231; Vieweg.

* cited by examiner

*Primary Examiner* — Brian Q Le
*Assistant Examiner* — Jose M Torres (57) ABSTRACT

The invention relates to a method for the joint of registering, archiving, contrast-retaining merging, and visualizing of 2D x-ray images and reconstructed 2D projections or 3D views of generated image data in minimally invasive medical interventions or operations performed under x-ray control on internal organs, areas of tissue, lesions, or pathological structures in a patient's body. A first image and the image data of a second image being mixed over the first image are mutually linked, co-registered, and merged using an alpha-channel-based mixing technique, whereby the color values or gray-scale values of the individual pixels of the first image are prior to being mixed-over with the segmented foreground of the second image brightened through the application of a color-value or gray-scale-value for compensating or lessening the reduction in contrast that occurs during mix-over in the first image before being displayed graphically on a monitor terminal.

9 Claims, 3 Drawing Sheets

IMAGE SYSTEM FOR RETAINING CONTRAST WHEN MERGING IMAGE DATA

CROSS REFERENCE TO RELATED APPLICATIONS

This application claims priority of German application No. 10 2007 021 035.5 filed May 4, 2007, which is incorporated by reference herein in its entirety.

FIELD OF THE INVENTION

The present invention relates to a method performed using an image-processing, image-visualizing, and image-archiving system that can be employed particularly in the area of diagnostic and interventional radiology for the joint registering, archiving, contrast-retaining merging, and visualizing of 2D x-ray images and reconstructed 2D projections or, as the case may be, 3D views of generated image data required within the scope of, for instance, minimally invasive medical interventions or operations performed under x-ray control on internal organs, areas of tissue, lesions, or pathological structures in a patient's body.

BACKGROUND OF THE INVENTION

For navigating the medical instruments required during a medical intervention, 2D x-ray images generated in realtime using fluoroscopic imaging of the sites being treated and of the areas of internal tissue surrounding them in a patient undergoing treatment are evaluated. Although showing no spatial details, in contrast to 3D views reconstructed from two-dimensional projection data of a number of axial 2D cross-sectional images combined into one volume dataset having been obtained by means of, for example, spiral CT or rotation angiography, two-dimensional x-ray images are nonetheless available in realtime and enable both the doctor's and patient's exposure to radiation to be minimized because the patient needs to be x-rayed just once from a single irradiating direction.

The spatial depth information is conventionally retrieved by merging 2D x-ray images recorded using fluoroscopic imaging with 3D reconstructions of preoperatively generated CT or MRT cross-sectional images of the regions of the body being treated and areas of tissue surrounding them or, as the case may be, with intraoperatively recorded 3D rotation angiograms, and registering them together therewith. Merging therein involves an image-processing procedure whereby three-dimensionally reproduced image objects are rendered congruent with the relevant image objects in recorded 2D x-ray images and additively superimposed thereon. The image objects that have been three-dimensionally reconstructed or recorded in three-dimensional form using rotation angiography are therefore placed under two-dimensional fluoroscopic x-ray images whose image data is then stored (co-registered) in an image archive along with the image data of the image objects that have been three-dimensionally reconstructed or, as the case may be, recorded in three-dimensional form. Combining co-registered 2D layer recordings and three-dimensionally reconstructed image objects therein makes it easier for doctors providing treatment to find their bearings within a volume area under consideration.

Registering and visualizing of the merged 2D and 3D image data is therein usually performed in two separate steps: It must first be ascertained from which direction a volume area requiring to be imaged has to be projected so it can be rendered congruent with a 2D x-ray image recorded by means of, for example, an angiography system and registered jointly with said image. For that there are various possible approaches which though, having no relevance to the subject matter of the present invention, can be left out of account. The co-registered image data must during visualizing be displayed in a merged 2D/3D representation, which is to say in a joint representation of a recorded 2D x-ray image F (referred to below also as a "fluoroscopy image") and of a 3D reconstruction M projected into the representation plane $E_{xy}$ (projection plane) of the relevant 2D x-ray image, which reconstruction will then of course also be two-dimensional.

A standard method for jointly graphically visualizing the image data of two or more initial images is what is termed "overlaying". The respective initial images are therein rendered mutually congruent and overlaid ("cross-mixed") to form an aggregate image by means of alpha blending—a digital image- or video-processing technique—taking account of the individual pixels' respective color and transparency information. For various graphic formats (for example PNG, PSD, TGA, or TIFF), what is termed an alpha channel is provided therefor in which, besides the actual image data's coded color information, transparency information is stored using m-bit coding in up to $2^m$ gradations, able to be indicated by means of an opacity value $\alpha$ (blending factor) in the range between zero (totally transparent) and one (totally opaque). A merged 2D aggregate image B created by means of alpha blending when the two two-dimensional images F and M are overlaid can be described in mathematical terms as a three-dimensional field (meaning as a third-order tensor) with components having the form $(n_x, n_y, I_B(n_x, n_y))$, which is to say as a triplet, with $n_x$ and $n_y$ being the x and y coordinates of the individual pixel locations in the image plane $E_{xy}$ of the merged aggregate image B and $I_B(n_x, n_y)$ being the gray-scale or, as the case may be, RGB color values of the pixels at said image's relevant pixel locations. While the former instance is a special one-dimensional case where $I_B(n_x, n_y)$ can be described as a scalar quantity $I_B(n_x, n_y)$ indicating the intensity at the site of the respective pixel $(n_x, n_y)$, the latter instance with $I_B(n_x, n_y)$ is a three-dimensional color vector whose components describe the luminance values of the individual primary colors red, green, and blue of the merged aggregate image B at the site of a pixel $(n_x, n_y)$. Said vector can therein be calculated using the formula $$I_B(n_x,n_y):=\alpha \cdot I_M(n_x,n_y)+(1-\alpha)\cdot I_F(n_x,n_y) \forall (n_x,n_y) \qquad (1)$$

where $0<\alpha<1$, with $I_F(n_x, n_y)$ or, as the case may be, $I_M(n_x, n_y)$ likewise being vector quantities indicating the color values of the pixels at the relevant pixel locations $(n_x, n_y)$ of the two images and with the scalar factor $\alpha$ indicating the opacity value used (referred to below also as the "blending factor"). That is a special form of linear combining, known as "conical affine combining", where all coefficients are greater than zero and add up to one (convex combining). The blending factor $\alpha$ is therein a parameter describing what percentage of the gray-scale values of the individual pixels of the merged aggregate image B each of the two overlaid initial images F and M is to occupy.

What, though, is disadvantageous about that method is that image objects (such as ends of catheters and cardiovascular stent implants etc.) shown in the fluoroscopy image F with a low contrast definition will upon mixing-over of a 3D reconstruction M that is projected into the projection plane $E_{xy}$ of the relevant fluoroscopy image F and has a high contrast definition be virtually obscured by said reconstruction when a blending factor close to one is employed. The image contrast $K_B$, which can be shown as a function of $\alpha$, is in the one-dimensional, scalar instance therein defined by the formula $$K_B(\alpha) := \frac{I_{BH}(\alpha) - I_{BV}(\alpha)}{I_{BH}(\alpha)}, \qquad (2)$$

with $I_{BV}$ being the image intensity of an image object BO in the foreground BV of the merged aggregate image B and $I_{BH}$ being the image intensity of an object background BH, obscured by the relevant image object BO, on said image. If the image object BO shown in the foreground MV of the overlying image M can be segmented from the background MH of said overlay image M (which can as a rule be easily achieved by way of a threshold decision), it is customarily provided for only the segmented image object BO to be overlaid on the fluoroscopy image F. It is thereby insured that in the merged aggregate image B the contrast definition of the fluoroscopy image F will be retained at least in the background region BH of the mixed-in segmented image object BO. That does not, though, apply to the foreground region BV of the merged aggregate image B because the contrast definition reduces there owing to overlaying of the two initial images F and M.

A known way to retain the contrast definition also in the foreground region BV, defined by the area of the image object BO, of the merged aggregate image B is to mix only the outline of the image object BO segmented from the background MH of the overlay image M into the fluoroscopy image F. That, though, is expedient for a few applications only. Moreover, the 3D impression of the segmented and mixed-in image object BO and the information indicating that the segmented image object BO of the overlay image M is to form the foreground BV of the merged aggregate image B and that the areas of tissue, implants, or medical instruments (for example aspirating needles, catheters, surgical implements etc.) shown in the fluoroscopy image F are to form the background BH of the merged aggregate image B (or vice versa) are lost with that method. Another method provides for displaying the two initial images F and M not one above the other but laterally mutually displaced. That, though, has the disadvantage in some applications that the information indicating the spatial relationship between the segmented image object BO in the foreground BV of the merged aggregate image B and the areas of tissue and objects shown in the image background BH of the merged aggregate image B can be lost.

Another way to retain the contrast definition in the foreground region BV, defined by the area of the image object BO, of the merged aggregate image B is to segment the implants or medical instruments shown in the foreground FV of the fluoroscopy image F in order to overlay only said objects on the 3D view M projected into the projection plane $E_{xy}$ of the relevant fluoroscopy image F and on the image object BO shown in said view. Because the background FH of the fluoroscopy image F is with that method subtracted as a mask when segmenting has been performed, the areas of tissue imaged therein can no longer be shown in the merged aggregate image B. With a few exceptions that is very disadvantageous in most applications because the information about the exact spatial positioning of the implants or medical instruments that are shown in relation to the surrounding areas of tissue is lost. That method will, moreover, fail if the spatial positioning of the implants or medical instruments shown in the foreground FV of the fluoroscopy image F changes relative to the position of the areas of tissue shown in said image's background FH, for example because the mobile C-arm of a multidirectional C-arm x-raying system or the table on which the patient being examined is lying has been moved or, as the case may be, owing to the patient's moving or breathing or because his/her moving organs (such as the lungs or heart) have moved through pulsating. Standard alpha blending will remain the only option in such cases.

SUMMARY OF THE INVENTION

Proceeding from the above-cited prior art, the object of the present invention is to retain the contrast definition when fluoroscopic 2D x-ray recordings and reconstructed 2D projections or, as the case may be, 3D views of recorded image objects are overlaid, in order to increase the precision and safety of minimally invasive medical interventions or operations performed under x-ray control using merged and co-registered image data featuring the same imaging modality or, as the case may be, using merged and co-registered image data featuring different or different kinds of imaging modalities.

Said object is inventively achieved by means of the features of the independent claims. Advantageous exemplary embodiments that develop the concept underlying the invention are defined in the dependent claims.

The present invention relates according to a first aspect to an image-processing, image-visualizing, and image-archiving system that can be employed particularly in the area of diagnostic and interventional radiology for the joint registering, archiving, contrast-retaining merging, and visualizing of digital image data of at least two images. The inventive system therein has a merging, registering, and visualizing tool that mutually links, co-registers, and merges the image data of a first image, requiring to be mixed-over, and the image data of a second image being mixed over the first image using an alpha-channel-based mixing technique, then causes said data to be displayed graphically on a monitor terminal's display screen. The inventive merging, registering, and visualizing tool is therein designed such that with this mixing technique the color values or, as the case may be, gray-scale values of the first image's individual pixels will prior to being mixed-over with the second image's segmented foreground be brightened through the application of a color-value or, as the case may be, gray-scale-value term that compensates or lessens the reduction in contrast that occurs during mix-over in the first image, being mixed-over.

The merging, registering, and visualizing tool therein includes inter alia a module for performing a coordinate transformation by means of which identical image objects requiring to be overlaid in the at least two images being merged will, if not already the case, be overlaid in such a way as to be exactly congruent. The merging, registering, and visualizing tool furthermore includes a module serving to segment the area formed by the image object, being mixed-in, in the foreground of the second image, being mixed-over, from the object background of said image and then to subtract the color values or, as the case may be, gray-scale values of the segmented object background from the color values or, as the case may be, gray-scale values of the aggregate image being mixed-over. The image data of the first image, requiring to be mixed-over, and the image data of the second image, being mixed over the first image, which sets of image data have been linked and jointly registered with the aid of the merging, registering, and visualizing tool, is then stored in merged form and/or separately in a specially provided memory unit belonging to the image-processing, image-visualizing, and image-archiving system.

According to a second aspect, the present invention relates to a method, executed by the image-processing, image-visualizing, and image-archiving system, for the joint registering, archiving, contrast-retaining merging, and visualizing of digital image data of at least two images. The method is characterized in that, employing an alpha-channel-based mixing technique whereby the color values or, as the case may be, gray-scale values of the first image's individual pixels are prior to being mixed-over with the second image's segmented foreground brightened through the application of a color-value or, as the case may be, gray-scale-value term compensating or lessening the reduction in contrast that occurs during mix-over in the first image, being mixed-over, the image data of a first image, requiring to be mixed-over, and the image data of a second image, being mixed over the first image is mutually linked, co-registered, merged, and caused to be displayed graphically on a monitor terminal's display screen.

The inventive method includes inter alia performing a coordinate transformation by means of which identical image objects requiring to be overlaid will, if not already the case, be overlaid in the at least two images being merged in such a way as to be exactly congruent. The method furthermore includes a step at which the image object requiring to be mixed-in is segmented in the foreground region of the second image, being mixed-over, from said image's object background and the color values or, as the case may be, gray-scale values of the segmented object background are then subtracted from the color values or, as the case may be, gray-scale values of the aggregate image being mixed-over. The linked and jointly registered image data of the first image, requiring to be mixed-over, and the image data of the second image, being mixed over the first image, is then stored in merged form and/or separately.

The color-value or, as the case may be, gray-scale-value term compensating or lessening the reduction in contrast when the two images are mixed-over can inventively be, for example, an image operator serving to invert the color values or, as the case may be, gray-scale values of the image requiring to be mixed-over, an additive color-value or, as the case may be, gray-scale offset dependent on the blending factor of the alpha-channel-based mixing technique, or a multiplicative color-value or, as the case may be, gray-scale factor dependent on said blending factor. It can in the second case therein be provided, for example, for the additive color-value or, as the case may be, gray-scale offset to be formed by means of a location-independent, constant offset or by means of an offset into which the color values or, as the case may be, gray-scale values of the individual pixels in the foreground of the image being mixed-over are entered multiplicatively. In the third case the multiplicative color-value or, as the case may be, gray-scale factor can consist of, for example, a factor into which the gray-scale values of the individual pixels in the foreground of the image being mixed-over are entered multiplicatively in standardized form.

Because the present invention is intended to be used particularly in the area of medical image-data processing, the merged, jointly registered, and graphically visualized image data can be on the one hand—as far as the image data of the image requiring to be mixed-over (or, as the case may be, which has been mixed-over) is concerned—image data of two-dimensional fluoroscopic x-ray recordings of organs requiring to be imaged or, as the case may be, areas of tissue in the body of a patient being examined, which recordings have been obtained using a fluoroscopic imaging process, and on the other hand—as far as the image data of the image being mixed-over is concerned—image data of reconstructed 2D projections or, as the case may be, 3D views (M) of the relevant organs or, as the case may be, areas of tissue, which projections or views are required, for example, within the scope of minimally invasive medical interventions or operations performed on internal organs, areas of tissue, lesions, or pathological structures in a patient's body.

According to a third aspect, the present invention relates to a computer-software-program product that is suitable for implementing the described method when operated on a monitor terminal belonging to the above-described image-processing, image-visualizing, and image-archiving system.

BRIEF DESCRIPTION OF THE DRAWINGS

Further features of the present invention will emerge from the dependent claims and from the description of exemplary embodiments illustrated in the following drawings.

DETAILED DESCRIPTION OF THE INVENTION

The system components of the inventive image-processing, image-visualizing, and image-archiving system and the steps of the associated inventive method are described in detail in the following sections with the aid of the attached drawings.

Figure 1:
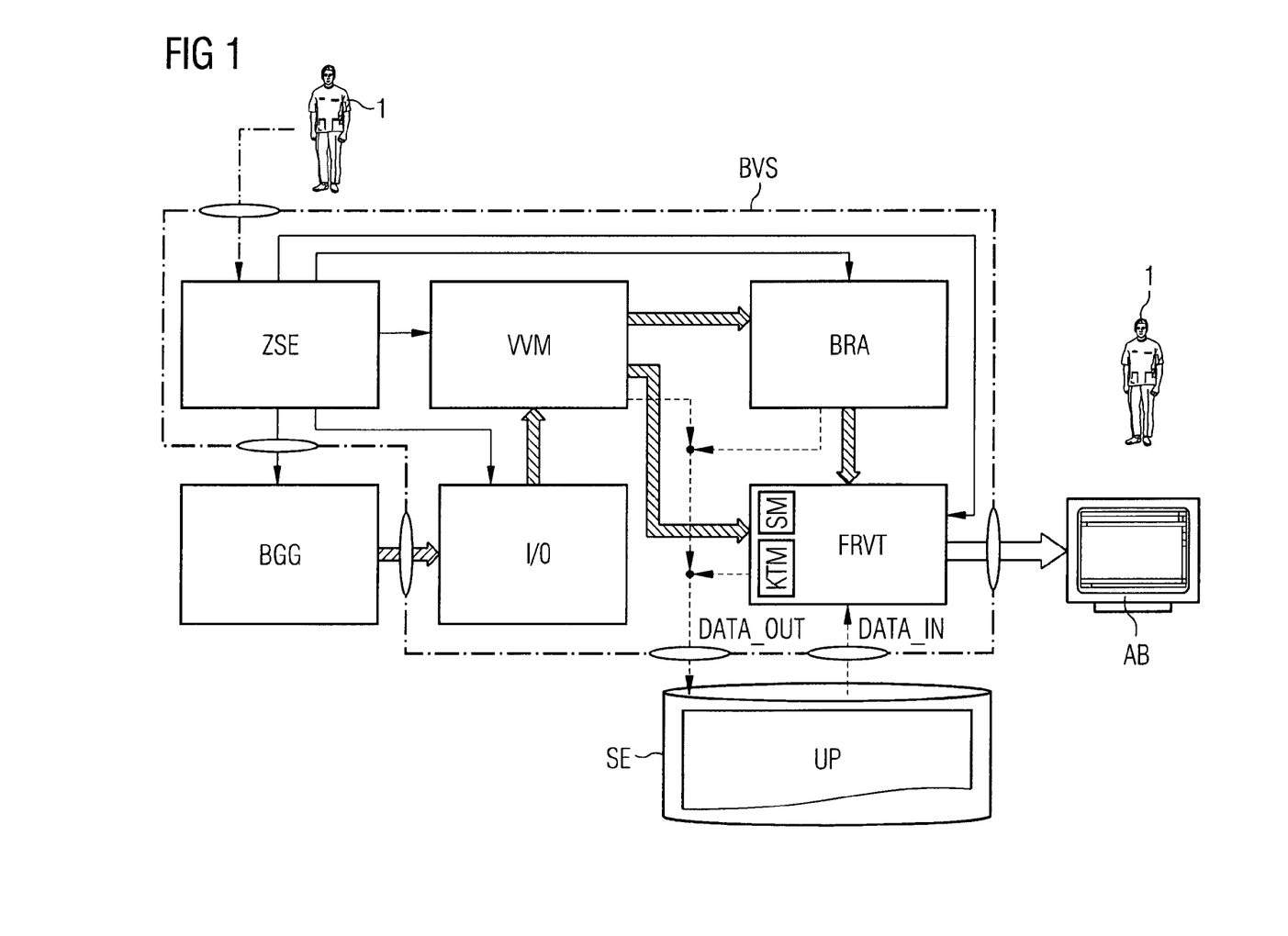
FIG. 1 is a block diagram of an image-processing, image-visualizing, and image-archiving system according to the present invention, which system is used for the joint registering, archiving, contrast-retaining merging, and visualizing of fluoroscopic 2D x-ray images and reconstructed 2D projections or, as the case may be, 3D views of generated CT or, as the case may be, MRT image data.

FIG. 1 is a schematic block diagram of an image-processing, image-visualizing, and image-archiving system according to the present invention, which system makes it possible to jointly log, register, and archive image data—generated by a medical imaging device BGG such as, for example, an angiography system—relating to internal organs, areas of tissue of interest, pathological structures, medical implants, and other objects in the body of a patient being examined, in the form on the one hand of fluoroscopic 2D x-ray recordings and on the other of reconstructed 2D projections shown from any projection angles or reconstructed 3D views and to visualize it in the form of merged graphical presentations on a monitor terminal's display screen AB.

As sketched in FIG. 1, the image data generated by, for example, an angiographic imaging process is routed via an input/output interface I/O to an image-processing system BVS. Apart from a central control device ZSE that controls the exchange of data with the imaging device BGG and the exchange of data between the individual system components of the image-processing system BVS, the image-processing system BVS can therein include inter alia a pre-processing module VVM having a digital filter for suppressing noise, improving the contrast, and detecting edges. A 2D/3D image-rendering application BRA integrated in the image-processing system BVS serves to generate reconstructed 2D projections and/or 3D views and graphically visualize the areas of tissue requiring to be imaged. The image-processing system BVS furthermore also includes a merging, registering, and visualizing tool FRVT that is linked at its input side to the data outputs of the pre-processing module VVM and 2D/3D image-rendering application BRA and whose precise function will be explained further below.

Whenever image data is generated by the imaging device BGG and made available via an input interface to the image-processing system BVS, at the instigation of the central control device ZSE it can on completion of pre-processing be stored for later graphic visualizing temporarily or permanently, depending on the system configuration, in an image-data memory of an external memory unit SE, where it will be written to a patient-specific examination log UP of a log file kept in a memory area of the memory unit SE. It is also possible alongside the image data obtained within the scope of the angiographic imaging process to write all recording parameters set manually by a radiologist 1 performing the examination and all representation and reconstruction parameters required for visualizing reconstructed 2D projections or, as the case may be, 3D views of specific areas within the patient's body in a standardized data format (the DICOM format, for example) via a data-output interface DATA_OUT of the image-processing system BVS to the patient-specific examination log UP of the externally stored log file. The stored image data and recording and reconstruction parameters can for graphic visualizing be loaded into a local temporary memory (not shown) of the merging, registering, and visualizing tool FRVT via a data-input interface DATA_IN of the image-processing system BVS.

As can be seen from FIG. 1, on the one hand the image data—obtained by means of fluoroscopic imaging and filtered by the pre-processing module VVM—of two-dimensional fluoroscopic x-ray images of areas of tissue being examined and, on the other, image data of reconstructed 2D projections generated with the aid of the 2D/3D image-rendering application BRA or, as the case may be, 3D views from within the body of the patient who has been examined under x-ray control is routed to the merging, registering, and visualizing tool FRVT, which data is then merged, linked, jointly registered, and graphically visualized on the monitor terminal's display screen AB using one of the mix-over techniques (see variants Nos. 1 to 4 of the method) described below. The image data of the merged images is for archiving written via the data-output interface DATA_OUT, cited in the introduction, of the image-processing system BVS (using, for example, the DICOM format) to the patient-specific examination log UP of the log file kept in the external memory unit SE and stored retrievably and permanently in said log.

As described above, image data—co-registered with the aid of the merging, registering, and visualizing tool FRVT—of a recorded 2D x-ray image F (for example image data of a 2D x-ray image generated by means of fluoroscopic imaging) and of a 3D reconstruction M (overlay image) projected into the relevant 2D x-ray image's representation plane $E_{xy}$ (projection plane) can be jointly visualized within the scope of a merged 2D/3D representation B (aggregate image). The two initial images F and M therein (if necessary) first undergo a coordinate transformation through which identical image objects shown in the respective images will (if not already the case) be overlaid in such a way as to be exactly congruent. When the image objects shown in the foreground MV of the overlying image M have been segmented from the background MH of the relevant overlay image, during which process for example a threshold-based value-discriminating method may be used, and a mask formed by the image background MH has been subtracted from the original image M, the segmented image objects of the overlay image M are mixed into the fluoroscopy image F by using alpha blending to additively overlay it with the overlay image M cleared of its background MH. Four different variants of the method are therein inventively distinguished that are described in detail below. Which of said variants of the method is ultimately applied depends on the respective medical application or, more precisely, on whether a 3D impression of the overlaid image object BO is at all necessary.

The mix-over techniques proposed within the scope of the present invention and to be implemented with the aid of the merging, registering, and visualizing tool FRVT are described in detail below. For a simplified notation only the one-dimensional case will be considered herein where $I_F(n_x, n_y)$, $I_M(n_x, n_y)$ and hence $I_B(n_x, n_y)$ can be written as scalar quantities $I_F(n_x, n_y)$, $I_M(n_x, n_y)$ or, as the case may be, $I_B(n_x, n_y)$ describing the intensities of the gray-scale values at the site of the individual pixels $(n_x, n_y)$. The inventive method is not, though, restricted to that special case; it can be applied also to a generalized instance in the case of which the three cited quantities are each represented by three-dimensional color vectors whose components indicate the luminance values of the three primary colors red, green, and blue at the pixel locations $(n_x, n_y)$ of the relevant images F, M or, as the case may be, B.

According to a first variant of the inventive method, a variant referred to below as "inverse blending", the gray-scale values in the region—corresponding to the segmented foreground MV of an overlay image M requiring to be mixed-in—of a recorded fluoroscopy image F are inverted. The gray-scale values $I_F(n_x, n_y)$ of the relevant fluoroscopy image F are for all pixel locations $(n_x, n_y)$ therein replaced with the corresponding gray-scale values $I_F'(n_x, n_y)$ of the associated negative image F', which for m-bit coding can be shown thus:

$$I_F'(n_x,n_y):=I_{F,max}-I_F(n_x,n_y) \forall (n_x,n_y), \quad (3a)$$

where $I_{F,max}:=2^m-1 (m \in N)$. (3b)

The advantage of said first variant of the method is that the contrast definition of the fluoroscopy image F in the merged aggregate image B, whose gray-scale values can be calculated using the formula $$I_B(n_x,n_y):=\alpha \cdot I_M(n_x,n_y)+(1-\alpha) \cdot I_F'(n_x,n_y) \forall (n_x,n_y), \quad (3c)$$

where $0<\alpha<1$, is fully retained. Since, though, only the region of the segmented foreground MV of image M is mixed into the inverted fluoroscopy image F', the 3D information of the mixed-in image object BO, meaning the information about the spatial positional relationship between the image object BO and the areas of tissue, in the object background MH, shown in the overlay image M will be lost. Nor is it possible with present-day image-processing systems to adjustably mix the segmented foreground MV of the overlay image M over the inverted fluoroscopy image F'.

According to a second variant of the inventive method a fixed offset value $\Delta I_F$, multiplied by the blending factor $\alpha$, is added to the gray-scale values in the region of a recorded fluoroscopy image F corresponding to the segmented foreground MV of an overlay image M being mixed-in. The fluoroscopy image F in the relevant region is brightened thereby. The gray-scale values of the individual pixel locations in the foreground region (Fe) and background region (FH$^+$) of the brightened fluoroscopy image F$^+$ obtained during that operation can be given thus:

$$I_{FV}^+(n_x,n_y):=I_{FV}(n_x,n_y)+\alpha \cdot \Delta I_F \forall (n_x,n_y) \in FV \text{ and} \quad (4a)$$

$$I_{FH}^+(n_x,n_y):=I_{FH}(n_x,n_y)+\alpha \cdot \Delta I_F \forall (n_x,n_y) \in FH, \quad (4b)$$

where $0<\alpha<1$

The advantages of said second variant of the method are that the contrast definition of the fluoroscopy image F in the merged aggregate image B, whose gray-scale values can be calculated using the formula $$I_B(n_x,n_y):=\alpha \cdot I_M(n_x,n_y)+(1-\alpha)\cdot I_F^+(n_x,n_y) \forall (n_x,n_y), \quad (4c)$$

where $0<\alpha<1$, and $$I_F^+(n_x, n_y) := \begin{cases} I_{FV}^+(n_x, n_y) \forall (n_x, n_y) \in FV \\ I_{FH}^+(n_x, n_y) \forall (n_x, n_y) \in FH, \end{cases} \quad (4d)$$

is at least approximately retained and that the segmented foreground MV of the overlay image M can be adjustably mixed over the brightened fluoroscopy image $F^+$. Since, though, only the region of the segmented foreground MV of image M is mixed into the brightened fluoroscopy image $F^+$, the 3D information of the mixed-in image object BO, meaning the information about the spatial positional relationship between the image object BO and the areas of tissue, in the object background MH, shown in the overlay image M will, as in the case of the first variant of the method, be lost here, too. In the case of very bright masks and images having large brightness components and a low dynamic range, in the event of a multiplicity of value overflows having the form $$\exists (n_x,n_y) \in FV \cup FH: I_F^+(n_x,n_y) > I_{F,max} = 2^m-1, \quad (4e)$$

saturations can occur that will then reduce the contrast definition of the merged aggregate image B.

According to a third variant of the inventive method the gray-scale values of the image object BO imaged in the foreground MV of the overlying image M, multiplied by the blending factor α, are added to the gray-scale values in the area of a recorded fluoroscopy image F corresponding to the segmented foreground MV of an overlay image M being mixed-in (referred to below also as a "mask"). The fluoroscopy image F in the relevant area is thereby additively brightened by means of the gray-scale values of the overlay image M in the area of the image object BO. The gray-scale values of the individual pixel locations in the foreground region ($FV^{++}$) and background region ($FH^{++}$) of the brightened fluoroscopy image $F^{++}$ obtained during that operation can be given thus:

$$I_{FV}^{++}(n_x,n_y):=I_{FV}(n_x,n_y)+\alpha \cdot I_{MV}(n_x,n_y) \forall (n_x,n_y) \in FV \text{ and} \quad (5a)$$

$$I_{FH}^{++}(n_x,n_y):=I_{FH}(n_x,n_y)+\alpha \cdot I_{MV}(n_x,n_y) \forall (n_x,n_y) \in FH, \quad (5b)$$

where $0<\alpha<1$

The advantages of said third variant of the method are that the contrast definition of the fluoroscopy image F in the merged aggregate image B, whose gray-scale values can in this case be calculated using the formula $$I_B(n_x,n_y):=\alpha \cdot I_M(n_x,n_y)+(1-\alpha)\cdot I_F^{++}(n_x,n_y) \forall (n_x,n_y), \quad (5c)$$

where $0<\alpha<1$, and $$I_F^{++}(n_x, n_y) := \begin{cases} I_{FV}^{++}(n_x, n_y) \forall (n_x, n_y) \in FV \\ I_{FH}^{++}(n_x, n_y) \forall (n_x, n_y) \in FH, \end{cases} \quad (5d)$$

is at least approximately retained and that the segmented foreground MV of the overlay image M can be adjustably mixed over the brightened fluoroscopy image $F^{++}$. Contrary to the above-described first and second variant of the inventive method, the 3D impression of the mixed-in image object BO in the merged aggregate image B is retained here. However, in the case of very bright masks and images having large brightness components and a low dynamic range, in the event of a multiplicity of value overflows having the form $$\exists (n_x,n_y) \in FV \cup FH: I_F^{++}(n_x,n_y) > I_{F,max} = 2^m-1, \quad (5e)$$

saturations can occur that will then reduce the contrast definition of the merged aggregate image B.

According to a fourth variant of the inventive method a multiplicative factor $$\rho := (1+\alpha) \cdot \frac{I_{MV}(n_x, n_y)}{I_{MV,max}} \quad (6a)$$

that depends on the gray-scale values $I_{MV}(n_x, n_y)$ at the corresponding pixel locations in the foreground MV of the overlay image M (the "mask") in proportion to the maximum gray-scale value $I_{MV,max}$ within said area and on the blending factor α is applied to the gray-scale values in the area of a recorded fluoroscopy image F corresponding to the segmented foreground MV of an overlay image M being mixed-in. The fluoroscopy image F in the relevant area is thereby multiplicatively brightened by means of the gray-scale values of the overlay image M in the area of the image object BO. The quotient $I_{MV}(n_x, n_y)/I_{MV,max}$ is a value-standardized representation of the gray-scale value $I_{MV}(n_x, n_y)$ at the pixel location ($n_x$, $n_y$) of the mask M. The gray-scale values of the individual pixel locations in the foreground region ($FV^*$) and background region ($FH^*$) of the brightened fluoroscopy image $F^*$ obtained during that operation can be given thus:

$$I_{FV}^*(n_x,n_y):=\rho \cdot I_{FV}(n_x,n_y) \forall (n_x,n_y) \in FV \text{ and} \quad (6b)$$

$$I_{FH}^*(n_x,n_y):=\rho \cdot I_{FH}(n_x,n_y) \forall (n_x,n_y) \in FH, \quad (6c)$$

where $0<\alpha<1$

The advantages of said fourth variant of the method are that the contrast definition of the fluoroscopy image F in the merged aggregate image B, whose gray-scale values can be calculated using the formula $$I_B(n_x,n_y):=\alpha \cdot I_M(n_x,n_y)+(1-\alpha)\cdot I_F^*(n_x,n_y) \forall (n_x,n_y), \quad (6d)$$

where $0<\alpha<1$, and $$I_F^*(n_x, n_y) := \begin{cases} I_{FV}^*(n_x, n_y) \forall (n_x, n_y) \in FV \\ I_{FH}^*(n_x, n_y) \forall (n_x, n_y) \in FH, \end{cases} \quad (6e)$$

is at least approximately retained and that the segmented foreground MV of the overlay image M can be adjustably mixed over the brightened fluoroscopy image $F^*$. Contrary to the above-described first and second variant of the inventive method, the 3D impression of the mixed-in image object BO in the merged aggregate image B is retained here also. However, in the case of very bright masks and images having large brightness components and a low dynamic range, in the event of a multiplicity of value overflows having the form $$\exists (n_x,n_y) \in FV \cup FH: I_F^*(n_x,n_y) > I_{F,max} = 2^m-1, \quad (6f)$$

saturations can occur that will then reduce the contrast definition of the merged aggregate image.

Figure 2:
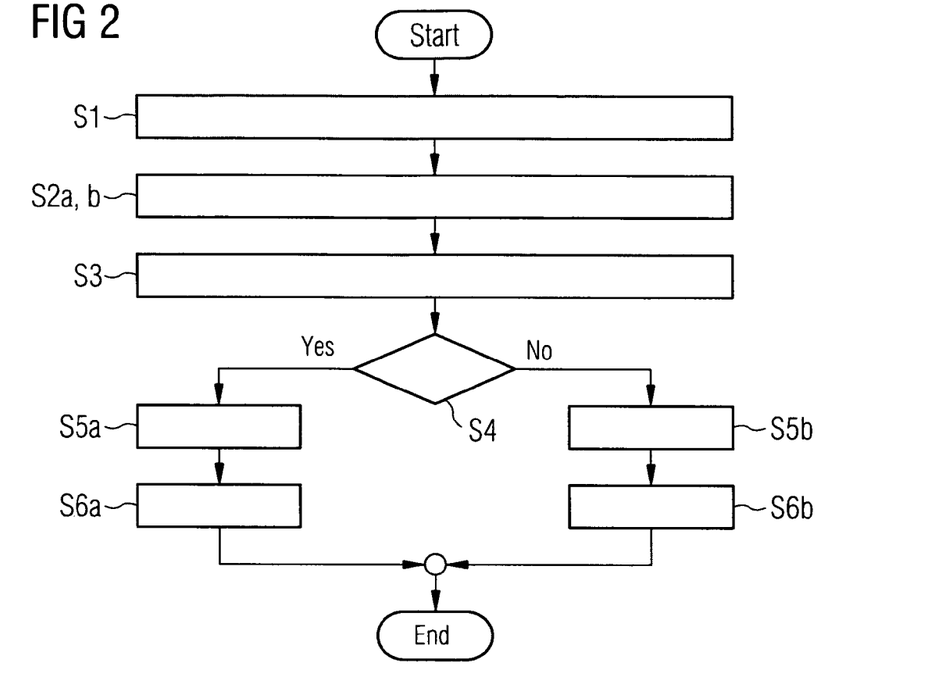
FIG. 2 is a flowchart serving to illustrate the inventive method for the joint registering, archiving, contrast-retaining merging, and visualizing of fluoroscopic 2D x-ray images and reconstructed 2D projections or, as the case may be, 3D views of generated CT or, as the case may be, MRT image data.

FIG. 2 is a flowchart serving to illustrate the inventive method. When the image data, generated by a medical imaging device (for example an angiography system), of an organ or area of tissue requiring to be imaged in the body of a patient being examined has been made available (S1), the image data obtained is routed over a high-speed data line to the input/ output interface I/O of the image-processing system BVS (S2a) and subjected in a module VVM provided therefor to a pre-processing procedure consisting in, for example, filtering (S2b) of the image data obtained for suppressing noise and detecting edges. A 2D/3D image-rendering application BRA is then applied (S3) to the obtained and filtered image data of the individual layer recordings which converts it into image data of reconstructed 2D projections that can be displayed at any projection angles and/or into image data of reconstructed 3D views. With the merging function activated, which is determined through a query (S4), the image data of obtained (F) and reconstructed images (M) is then at a step S5a jointly registered, archived, and merged by being mixed over. The two initial images F and M will, if necessary, first have been subjected to a coordinate transformation (not shown in FIG. 2) by means of which identical image objects shown in the respective images will (if not already the case) be overlaid in such a way as to be exactly congruent. For example one of the mix-over techniques described above with reference to one of the variants No. 1 to No. 4 of the method can be inventively employed for mixing over the two images F and M. It should therein be assumed here, too, that only the image foreground MV remaining in the overlay image M after the segmented background MH has been subtracted, meaning the part of said image showing a reconstructed 2D projection or 3D view of an image object BO in the patient's body, which object requires to be displayed, will be mixed into a 2D x-ray recording F, generated by means of fluoroscopic imaging, of the surrounding areas of tissue of said image object BO. The merged image data is then displayed graphically on a display screen AB of a monitor terminal (S6a). If, though, the response to the query at step S4 is that the merging function has not been activated, the obtained and reconstructed image data will at a step S5b first be separately registered and archived before the relevant image data is separately displayed graphically on the monitor terminal's display screen AB (S6b).

Figure 3:
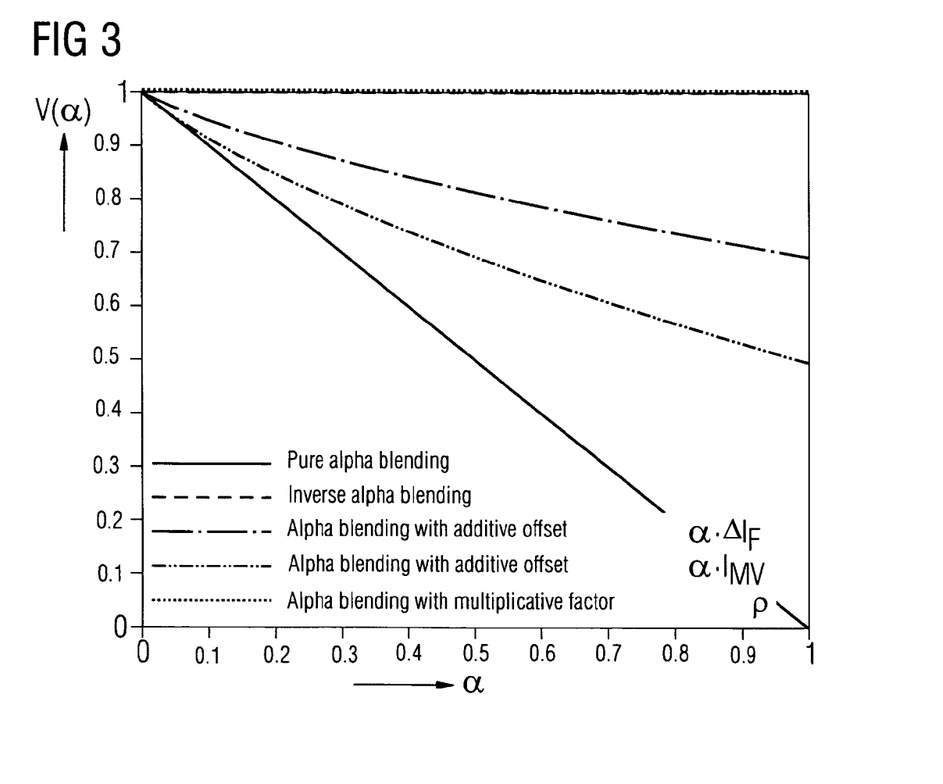
FIGS. 3 to 5 are three diagrams by means of which the inventive method's individual variants are mutually contrasted and compared in terms of their contrast retention for different parameter values.
Figure 4:
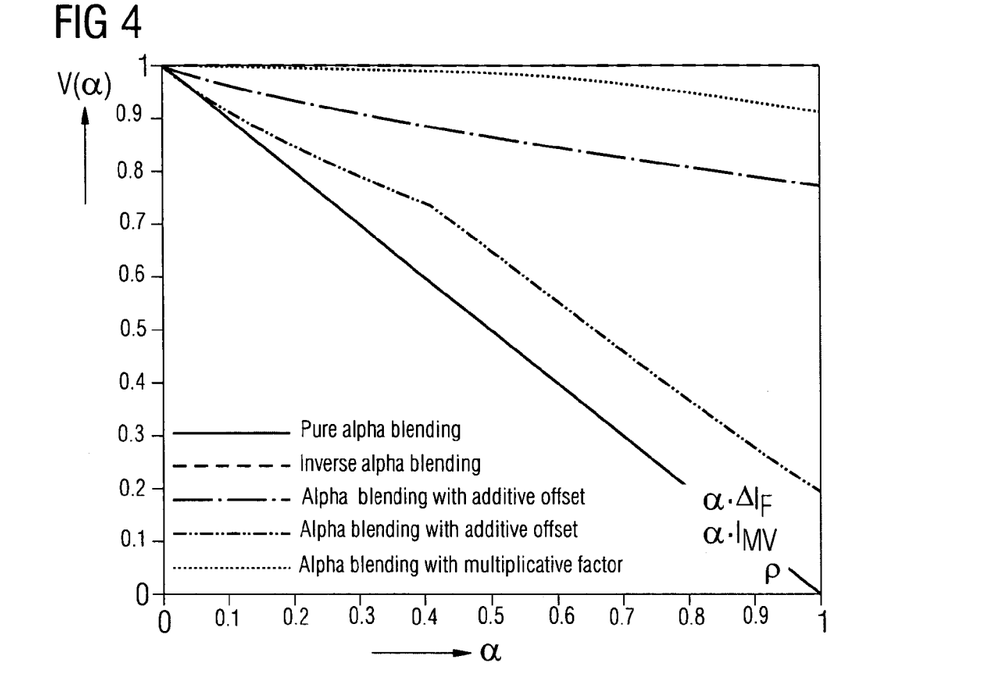
Figure 5:
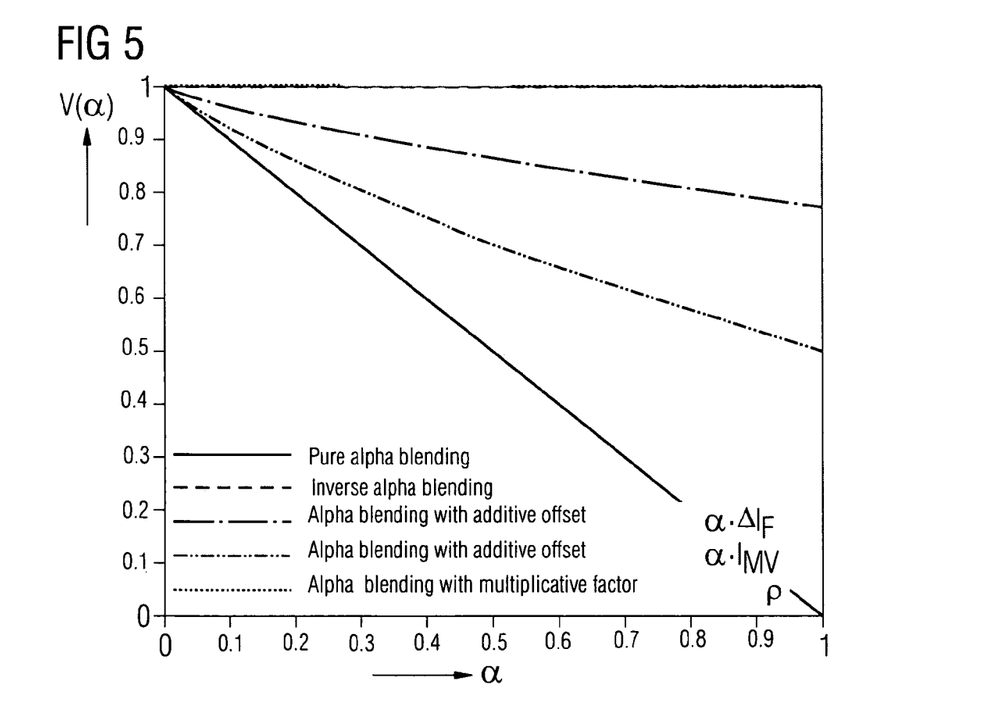

FIGS. 3 to 5 are three diagrams by means of which the inventive method's individual variants are mutually contrasted and compared in terms of their contrast retention for different parameter values. The ratio V between, on the one hand, the image contrast that can be achieved using one of the four variants of the method and is produced on mixing a segmented image object BO forming the foreground region MV of an overlay image M into a fluoroscopy image F generated by means of, for instance, angiographic imaging and, on the other, the original contrast definition of said fluoroscopy image F is therein in each case plotted over the values within the range 0 to 1 of the blending factor α along with the contrast ratio V that can be achieved on the region MV when conventional alpha blending is used compared with the original contrast definition of the fluoroscopy image F. Using the definition, given in formula (2), of the contrast definition $K_B$ for the merged aggregate image B and applying a corresponding formula $$K_F := \frac{I_{FH} - I_{FV}}{I_{FH}}, \qquad (7)$$

which gives the original contrast definition $K_F$ for the fluoroscopy image F, said contrast ratio can be given as a function of the blending factor α thus:

$$V(\alpha) := \frac{K_B(\alpha)}{K_F} = \frac{I_{FH}}{I_{FH} - I_{FV}} \cdot \frac{I_{BH}(\alpha) - I_{BV}(\alpha)}{I_{BH}(\alpha)}. \qquad (8a)$$

Since, as already mentioned, only the segmented image object BO in the foreground MV of the overlay image M is mixed into the fluoroscopy image F, $I_{BH}(\alpha)$ in formula (8a) can be replaced with $I_{FH}$, as a result of which the formula can be simplified to the following:

$$V(\alpha) = \frac{I_{FH} - I_{BV}(\alpha)}{I_{FH} - I_{FV}}. \qquad (8b)$$

Depending on which mixing technique is applied (pure alpha blending, inverse alpha blending, alpha blending with a fixed, additive offset $\Delta I_F$, alpha blending with additive incorporating of the overlay image M or, as the case may be, alpha blending with multiplicative incorporating of the gray-scale value-standardized overlay image), the terms given in the formulas (1), (3c), (4c), (5c) or, as the case may be, (6d) are therein to be used for $I_B$ for $I_{BV}(\alpha)$. Thus, for example, for the simplifying assumption of constant gray-scale values for all pixels in the foreground region ($F_V$) and background region (FH) of the fluoroscopy image F and for the assumption of constant gray-scale values for all pixels in the foreground region (MV) of the overlay image M for the parameter values $I_{FV}=60$, $I_{FH}=120$ and $I_{MV}=120$, the result is the functional equation below $$V(\alpha)=1-\alpha, \qquad (8c)$$

which is dependent only on the blending factor and is shown in FIGS. 3 to 5 as a descending straight line within the definition range αε]0; 1 [under consideration. As shown in FIGS. 3 to 5, said straight line crosses the abscissa at point (1; 0) and the ordinate at point (0; 1) of the respective diagram, specifically at a 45° angle in each case. The functional equations of all other function graphs of the families of curves sketched in FIGS. 3 to 5 can also be calculated analogously, with the parameter values $I_{FV}=60$, $I_{FH}=120$, $I_{MV}=120$ respectively for the gray-scale values in the foreground region (FV) and background region (FH) of the fluoroscopy image F and for the gray-scale values in the foreground region (MV) of the overlay image M as well as the parameter value $\Delta I_F=50$ for the gray-scale value offset in the foreground region (FV) of the fluoroscopy image F having been used by way of example for the diagram sketched in FIG. 3 and the parameter values $I_{FV}=30$, $I_{FH}=180$, $I_{MV}=180$ and $\Delta I_F=50$ for the graphs sketched in FIG. 4 and FIG. 5. The two diagrams in FIGS. 4 and 2c therein differ in that for the example sketched in FIG. 5 the displayable range of gray-scale values has been quantized using m=10 bits, representing a relatively large dynamic range of $2^{10}=1,024$ different gray-scale values, while for the example sketched in FIG. 4 the displayable range of gray-scale values has been quantized using m=8 bits, representing a relatively small dynamic range of $2^8=256$ different gray-scale values. Owing to said smaller dynamic range, disruptive saturation effects will occur in the latter instance that greatly diminish the contrast of the merged aggregate image B, a fact that can readily be seen by, for example, comparing the function graphs shown with a double dot-and-dash line in the diagrams in FIG. 4 and FIG. 5, which relate to the third variant of the method (additive incorporating of the overlay image M in calculating the merged aggregate image B). Said disruptive saturation effects can, though, be eliminated by specifying a suitably large dynamic range and a forced minimum distance between the foreground (BV) and background (BH) of the merged aggregate image B.

As can be seen in FIGS. 3 to 5, the imaged curve families' function graphs belonging to the individual variants of the method each exhibit a monotonically falling shape, with the point (0; 1) being in all three graphs a common fixed point of all curves in a family. The curves of the function graphs belonging to variants No. 2 (alpha blending with a fixed, additive offset $\alpha \cdot \Delta I_F$) and No. 3 (alpha blending with additive incorporating of the overlay image M) of the method are therein hyperbolic in shape and asymptotically approach the abscissa towards greater values for $\alpha$. Towards smaller values for $\alpha$ the rise of said function graphs increasingly approaches the rise $dV/d\alpha = -1$ of a straight line g given by the function rule (8c) for the contrast ratio $V(\alpha)$ of a pure alpha blending operation: $\alpha \mapsto V(\alpha) = 1 - \alpha$. As can further be seen from FIGS. 3 to 5 the contrast ratio $V(\alpha)$ is greatest for all values of the blending factor $\alpha$ in the case of variant No. 1 (inverse alpha blending) of the method because the curve shape of $V(\alpha)$ coincides for that case with a straight line h passing through the point (0; 1) and running parallel to the abscissa: $\alpha \mapsto V(\alpha) = 1$, and keeps reducing in the sequence of the above-described variants No. 4 (alpha blending with multiplicative incorporating of the overlay image M), No. 2 (alpha blending with a fixed, additive offset $\alpha \cdot \Delta I_F$), and No. 3 (alpha blending with additive incorporating of the overlay image M) of the method. The contrast ratio $V(\alpha)$ is lowest, and for all possible values in the definition range of the blending factor $\alpha$ moreover, when pure alpha is performed.

As a result of the above-mentioned saturation effects occurring when small dynamic ranges are employed, a curve shape with a downward kink at about $\alpha = 0.40$ is shown in FIG. 4 for the curve-family function graph belonging to variant No. 3 (alpha blending with additive incorporating of the overlay image M) of the method. A similar characteristic can also be observed for the curve-family function graph belonging to variant No. 4 (alpha blending with multiplicative incorporating of the overlay image M) of the method, the curve shape of which graph has a downward kink at about $\alpha = 0.44$.

The advantage of the inventive method is that the in any event already weak contrast of recorded 2D fluoroscopy images F can with the aid of the above-described mix-over techniques be retained despite the overlaying of mixed-in image objects BO. It is thus insured with the aid of said techniques that the discernibility of the catheters, implants, or medical instruments imaged in a fluoroscopic x-ray recording will not be impaired through merging and joint visualizing with CT or MRT cross-sectional images or with reconstructed 3D views or, as the case may be, 2D projections of image objects in a patient's body that are required to be shown.

The invention claimed is:

1. An image system for retaining a contrast when merging image data of at least two images of a patient, comprising:
    apparatus for receiving and processing images;
    an image processing unit operating within the apparatus that:
        mixes image data of a second image of the patient over with image data of a first image of the patient using an alpha-channel-based mixing technique,
        determines a compensating pixel value term for compensating a reduction of the contrast occurring during the mix-over, and
        brightens pixel values of the first image prior to being mixed-over with a foreground region of the second image by applying the compensating pixel value term for retaining the contrast according to the formulas:

$$I_{FV}^+(n_x,n_y) := I_{FV}(n_x,n_y) + \alpha \cdot \Delta I_F \forall (n_x,n_y) \in FV; \text{ and}$$

$$I_{FH}^+(n_x,n_y) := I_{FH}(n_x,n_y) + \alpha \cdot \Delta I_F \forall (n_x,n_y) \in FH;$$

wherein
$\alpha$ is a blending factor $0 < \alpha < 1$;
$I_{FV}(n_x, n_y)$ means an intensity of a pixel at coordinates $(n_x, n_y)$ in a foreground region FV of the first image;
$I_{FH}(n_x, n_y)$ means an intensity of a pixel at coordinates $(n_x, n_y)$ in a background region FH of the first image;
$\Delta I_F$ is an offset value; and
"intensity" means a grey-scale value or a color luminance value.

2. A method implemented by a computer software program operating an image processing apparatus, the method comprising:
    receiving image data of a first image of a patient and image data of a second image of the patient into the image processing apparatus from an imaging device;
    mixing the image data of the second image of the patient over with the image data of the first image of the patient using an alpha-channel-based mixing technique,
    determining a compensating pixel value term for compensating a reduction of the contrast occurring during the mix-over, and
    brightening pixel values of the first image prior to being mixed-over with a foreground region of the second image by applying the compensating pixel value term for retaining the contrast according to the formulas:

$$I_{FV}^+(n_x,n_y) := I_{FV}(n_x,n_y) + \alpha \cdot \Delta I_{F\_} \forall (n_x,n_y) \in FV$$

$$I_{FH}^+(n_x,n_y) := I_{FH}(n_x,n_y) + \alpha \cdot \Delta I_{F\_} \forall (n_x,n_y) \in FH;$$

wherein
$\alpha$ is a blending factor $0 < \alpha < 1$;
$I_{FV}(n_x, n_y)$ means an intensity pixel at coordinates $(n_x, n_y)$ in a foreground region FV of the first image;
$I_{FH}(n_x, n_y)$ means an intensity of a pixel at coordinates $(n_x, n_y)$ in a background region FH of the first image;
$\Delta I_F$ is an offset value; and
"intensity" means a grey-scale value or a color luminance value; and
displaying the aggregate image on a monitor terminal attached to the image processing apparatus.

3. A method for retaining a contrast when merging image data of at least two images of a patient, comprising:
    receiving image data of a first image and a second image into an apparatus for processing image data;
    mixing image data of the second image of the patient with image data of the first image of the patient creating an aggregate image using an alpha-channel-based mixing technique performed in the apparatus;
    determining a compensating pixel value term for compensating a reduction of the contrast occurring during the mix-over;
    brightening pixel values of the first image prior to being mixed-over with a foreground region of the second image by applying the compensating pixel value term for retaining the contrast according to the formulas:

$$I_{FV}^+(n_x,n_y) := I_{FV}(n_x,n_y) + \alpha \cdot \Delta I_F \forall (n_x,n_y) \in FV;$$

$$I_{FH}^+(n_x,n_y) := I_{FH}(n_x,n_y) + \alpha \cdot \Delta I_F \forall (n_x,n_y) \in FH;$$

wherein
$\alpha$ is a blending factor $0 < \alpha < 1$;
$I_{FV}(n_x, n_y)$ means an intensity of a pixel at coordinates $(n_x, n_y)$ in a foreground region FV of the first image;

$I_{FH}$ ($n_x$, $n_y$) means an intensity of a pixel at coordinates ($n_x$, $n_y$) in a background region FH of the first image;

$\Delta I_F$ is an offset value; and

"intensity" means a grey-scale value or a color luminance value; and displaying the aggregate image on a monitor terminal attached to the apparatus.

4. The method as claimed in claim 3, wherein the first image is a two-dimensional x-ray recording of the patient and the second image is a reconstructed 2D or 3D projection of the first image.

5. The method of claim 3, wherein the aggregate image is characterized by the formulas:

$$I_B(n_x,n_y):=\alpha \cdot I_M(n_x,n_y)+(1-\alpha)\cdot I_F^+(n_x,n_y) \forall (n_x,n_y),$$

wherein $0<\alpha<1$; and $$I_F^+(n_x, n_y) := \begin{cases} I_{FV}^+(n_x, n_y) \forall (n_x, n_y) \in FV \\ I_{FH}^+(n_x, n_y) \forall (n_x, n_y) \in FH \end{cases};$$

wherein $I_B$ ($n_x$, $n_y$) means an intensity of a pixel at coordinates ($n_x$, $n_y$) in the aggregate image;

$I_M$ ($n_x$, $n_y$) means an intensity of a pixel at coordinates ($n_x$, $n_y$) in the second image; and $I_F$ ($n_x$, $n_y$) means an intensity of a pixel at coordinates ($n_x$, $n_y$) in the first image.

6. A method for retaining a contrast when merging image data of at least two images of a patient, comprising:

receiving image data of a first image and a second image into an apparatus for processing image data;

mixing image data of the second image of the patient with image data of the first image of the patient creating an aggregate image using an alpha-channel-based mixing technique performed in the apparatus;

determining a compensating pixel value team for compensating a reduction of the contrast occurring during the mix-over;

brightening pixel values of the first image prior to being mixed-over with a foreground region of the second image by applying the compensating pixel value term for retaining the contrast according to the formulas:

$$I_{FV}^{++}(n_x,n_y):=I_{FV}(n_x,n_y)+\alpha \cdot I_{MV}(n_x,n_y) \forall (n_x,n_y) \epsilon FV; \text{ and}$$

$$I_{FH}^{++}(n_x,n_y):=I_{FH}(n_x,n_y)+\alpha \cdot I_{MV}(n_x,n_y) \forall (n_x,n_y) \epsilon FH;$$

wherein $\alpha$ is a blending factor $0<\alpha<1$;

$I_{FV}$ ($n_x$, $n_y$) means an intensity of a pixel at coordinates ($n_x$, $n_y$) in a foreground region FV of the first image;

$I_{MV}$ ($n_x$, $n_y$) means an intensity of a pixel at coordinates ($n_x$, $n_y$) in the foreground region of the second image;

$I_{FH}$ ($n_x$, $n_y$) means an intensity at coordinates ($n_x$, $n_y$) in a background region FH of the first image; and "intensity" means a grey-scale value or a color luminance value; and displace the aggregate image on a monitor terminal attached to the apparatus.

7. The method of claim 6, wherein the aggregate image is characterized by the formulas:

$$I_B(n_x,n_y):=\alpha \cdot I_M(n_x,n_y)+(1-\alpha)\cdot I_F^{++}(n_x,n_y) \forall (n_x,n_y),$$

wherein $0<\alpha<1$; and $$I_F^+(n_x, n_y) := \begin{cases} I_{FV}^+(n_x, n_y) \forall (n_x, n_y) \in FV \\ I_{FH}^+(n_x, n_y) \forall (n_x, n_y) \in FH \end{cases};$$

wherein $I_B$ ($n_x$, $n_y$) means an intensity of a pixel at coordinates ($n_x$, $n_y$) in the aggregate image;

$I_M$ ($n_x$, $n_y$) means an intensity of a pixel at coordinates ($n_x$, $n_y$) in the second image; and $I_F$ ($n_x$, $n_y$) means an intensity of a pixel at coordinates ($n_x$, $n_y$) in the first image.

8. A method for retaining a contrast when merging image data of at least two images of a patient, comprising:

receiving image data of a first image and a second image into an apparatus for processing image data;

mixing image data of the second image of the patient with image data of the first image of the patient creating an aggregate image using an alpha-channel-based mixing technique performed in the apparatus;

determining a compensating pixel value term for compensating a reduction of the contrast occurring during the mix-over;

brightening pixel values of the first image prior to being mixed-over with a foreground region of the second image by applying the compensating pixel value term for retaining the contrast according to the formulas:

$$\rho := (1+\alpha) \cdot \frac{I_{MV}(n_x, n_y)}{I_{MV,max}};$$

$$I_{FV}^*(n_x,n_y):=\rho \cdot I_{FV}(n_x,n_y) \forall (n_x,n_y) \epsilon FV; \text{ and}$$

$$I_{FH}^*(n_x,n_y):=\rho \cdot I_{FH}(n_x,n_y) \forall (n_x,n_y) \epsilon FH;$$

wherein $\alpha$ is a blending factor $0<\alpha<1$;

$I_{FV}$ ($n_x$, $n_y$) means an intensity of a pixel at coordinates ($n_x$, $n_y$) in a foreground region FV of the first image;

$I_{MV}$ ($n_x$, $n_y$) means an intensity of a pixel at coordinates ($n_x$, $n_y$) in the foreground region of the second image;

$I_{FH}$ ($n_x$, $n_y$) means an intensity of a pixel at coordinates ($n_x$, $n_y$) in a background region FH of the first image; and "intensity" means a grey-scale value or a color luminance value; and displaying the aggregate image on a monitor terminal attached to the apparatus.

9. The method of claim 8, wherein the aggregate image is characterized by the formulas:

$$I_B(n_x,n_y):=\alpha \cdot I_M(n_x,n_y)+(1-\alpha)\cdot I_F^*(n_x,n_y) \forall (n_x,n_y),$$

wherein $0<\alpha<1$; and $$I_F^*(n_x, n_y) := \begin{cases} I_{FV}^*(n_x, n_y) \forall (n_x, n_y) \in FV \\ I_{FH}^*(n_x, n_y) \forall (n_x, n_y) \in FH \end{cases};$$

wherein
$I_B(n_x, n_y)$ means an intensity of a pixel at coordinates $(n_x, n_y)$ in the aggregate image;
$I_M(n_x, n_y)$ means an intensity of a pixel at coordinates $(n_x, n_y)$ in the second image; and
$I_F(n_x, n_y)$ means an intensity of a pixel at coordinates $(n_x, n_y)$ in the first image.

\* \* \* \* \*